(12) United States Patent
Huth et al.

(10) Patent No.: US 7,514,255 B2
(45) Date of Patent: Apr. 7, 2009

(54) METHODS AND DEVICES FOR DETECTING PANCREATIC LIPASE

(75) Inventors: Stacey Pazar Huth, Yarmouth, ME (US); Marilyn I. Strong-Townsend, Yarmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 11/292,250

(22) Filed: Dec. 1, 2005

(65) Prior Publication Data

US 2006/0121549 A1    Jun. 8, 2006

Related U.S. Application Data

(60) Provisional application No. 60/633,114, filed on Dec. 3, 2004.

(51) Int. Cl.
*C12Q 1/34* (2006.01)
*C12M 1/34* (2006.01)

(52) U.S. Cl. ........................ 435/287.1; 435/18

(58) Field of Classification Search .................. 435/18, 435/287.1
See application file for complete search history.

(56) References Cited

U.S. PATENT DOCUMENTS

| | | | | |
|---|---|---|---|---|
| 3,992,158 | A | | 11/1976 | Przybylowicz et al. |
| 4,066,403 | A | * | 1/1978 | Bruschi ........................ 435/12 |
| 4,078,892 | A | * | 3/1978 | Steinbrink, Jr. ............... 436/97 |
| 4,428,907 | A | * | 1/1984 | Heijenga et al. .............. 422/61 |
| 4,769,333 | A | * | 9/1988 | Dole et al. ..................... 422/58 |
| H623 | H | * | 4/1989 | Miyazako ................... 436/170 |
| 4,988,497 | A | * | 1/1991 | Neumann et al. ............. 435/19 |
| 5,266,266 | A | | 11/1993 | Nason |
| 6,511,814 | B1 | | 1/2003 | Carpenter |
| 2002/0076742 | A1 | | 6/2002 | Chen et al. |
| 2003/0207333 | A1 | | 11/2003 | Steiner et al. |

FOREIGN PATENT DOCUMENTS

EP        0 526 226 A2  *  2/1993

OTHER PUBLICATIONS

Panteghini et al (2001) Measurement of pancreatic lipase activity in serum by a kinetic colorimetric assay using a new chromogenic substrate. Ann Clin Biochem 38: 365-370.*
Steiner JM et al (2003) Development and analytical validation of an enzyme-linked immunosorbent assay for the measurment of canine pancreatic lipase immunoreactivity in serum. Can J Vet Res 67: 175-182.*
Graca, R., et al., *Validation and diagnostic efficacy of a lipase assay using the substrate 1,2-o-dilauryl-rac-glycero glutaric acid-(6'methyl resorufin)-ester for the diagnosis of acute pancreatic in dogs*, Veterinary Clinical Pathology, 34:39-43 (2005).
Abstract—*Evaluation of Pancreas Specific Lipase Assay Utilizing the Substrate 1,2-O-Dilauryl-Rac-Glycero-3-Glutaric Acid-(6Methyl Resurofin)-Ester (GGR) for the Diagnosis of Canine Pancreatitis*, Society for Veterinary Clinical Pathology (ASVCP) 38th Annual Meeting, Veterinary Clinical Pathology, 32:151-156 (2003).
Instruction Manual, Coloripase, Product No. CL-700, NuClin Diagnostics, Inc.
Package Insert for Lipase Liquid, Application for Hitachi 717, Sentinel, Equal Diagnostics (Nov. 12, 1996).
Package Insert for Lipase Liquid, Application for Hitachi 747, Sentinel, Equal Diagnostics (Sep. 6, 1996).
Package Insert for Lipase Liquid, Sentinel, Equal Diagnostics (Jun. 16, 1999).
Package Insert for Lipase Color Liquid, Sentinel CH.
Package Insert for Lipase Colorimetric assay, Roche Diagnostics (2001).

* cited by examiner

*Primary Examiner*—Jon P Weber
*Assistant Examiner*—Kailash C Srivastava
(74) *Attorney, Agent, or Firm*—McDonnell Boehnen Hulbert & Berghoff LLP

(57) ABSTRACT

A method and device for determining pancreatic lipase in an animal blood sample. In one aspect, the device includes a compartmentalized container for storing and reacting the reagents for use in the assay. In another aspect, the device include a multilayer device having a spreading layer and reagents layers with dried reagents for detecting pancreatic lipase. The devices also includes a system for the optical determination of a color change in the reaction mixture. The method includes the use of the device to detect pancreatic lipase in samples.

39 Claims, No Drawings

METHODS AND DEVICES FOR DETECTING PANCREATIC LIPASE

PRIORITY INFORMATION

This application claims the benefit of U.S. Provisional Application Ser. No. 60/633,114 filed Dec. 3, 2004, which is incorporated by reference herein in its entirety.

BACKGROUND OF THE INVENTION

1. Field of the Invention

The invention relates to the field of veterinary medicine and more particularly to a device and method for detecting pancreatic lipase. The device and method may be used in the diagnosis and management of pancreatitis in animals.

2. Description of Related Art

Lipases are glycoprotein triglyceride hydrolases which catalyze the cleavage of triglycerides to diglycerides with subsequent formation of monoglycerides and fatty acids. Excess serum lipase is a symptom of pancreatitis, a disease of the pancreas characterized, in part, by excess lipase, protease and amylase production. Excess lipase production may, in turn, lead to numerous symptoms ranging from mild discomfort or death, depending, in part, on the severity of the disease and the extent of lipase overproduction.

Pancreatic lipases have for many years been important clinical chemistry parameters for the differential diagnosis of diseases of the pancreas. Numerous methods including enzymatic assays have been described for detecting lipase. Generally, however, these assays have had poor correlation between lipase activity determined in serum and the extent of damage to the pancreas. In particular, enzymatic assays for lipase have been found to be not specific enough to distinguish lipase activity originating from organs other than the pancreas.

Recently, a colorimetric test specific for pancreatic lipase in humans, based on the cleavage of a chromogenic lipase substrate 1,2-O-dilauryl-rac-glycero-3-glutaric acid-(6-methyl-rsorufin) ester ("DGGR"), has been described. For example, Lipase Colorimetric Assay reagents are available from Roche Diagnostics, GmbH (Mannheim Germany). This assay is sold as a kit with two separate reagents. The first reagent includes a buffer, and the DGGR substrate emulsified with a bile acid (taurodeoxy-cholate). The second reagent includes a buffer, a colipase and a cholate. The pancreatic lipase activity is determined specifically by the combination of the bile acid and the colipase used in the assay. Virtually no lipase activity is detected in the absence of the colipase. Colipase only activates pancreatic lipase, but not other lipolytic enzymes found in serum. The high amount of cholate ensures that the esterases present in the serum do not react with the chromogenic substrate due to the highly negative surface charge.

The DGGR substrate is cleaved by the catalytic action of the alkaline lipase solution to form 1,2-O-dilauryl- rac-glycerol and an unstable intermediate, glutaric acid-(6-methylresorufin) ester. This decomposes spontaneously in alkaline solution to form glutaric acid and methylresorufin. The color intensity of the red dye formed is directly proportional to the lipase activity and can be determined photometrically.

Other commercially available lipase assays include the Lipase Color Liquid assay from Sentinel Diagnostics, Milan, Italy, and the Coloripase Coloriometic Assay from Nuclin Diagnostics, Inc., Northbrook Ill.

The window for measurement of serum lipase is 14 days after an onset of acute pancreatitis, the peak of lipase activity reached within 24 hours and decreasing after 8 to 14 days. In animals, symptoms of pancreatitis are generally non-specific, with vomiting being the most common symptom presented to the clinician. This symptom, however, is indicative of many other diseases. Currently, animal testing for pancreatic lipase is performed at a reference laboratory remote from the clinic, which delays the diagnosis and, therefore, the treatment of the disease. Moreover, current calorimetric methods require automated or semi-automated diagnostic equipment to efficiently render a result. Rapid and specific clinic-based methods for pancreatic-specific lipase will allow rapid diagnosis and treatment of the patient.

SUMMARY OF THE INVENTION

In one aspect, the invention is directed to a method and a device for detecting the presence or amount of pancreatic lipase in an animal blood sample. The device includes a container having a first compartment containing a first reagent comprising a chromogenic lipase substrate, and a second compartment containing a second reagent comprising surface active agent. One or both of the first reagent and the second reagent include a colipase. The container stores the first and the second reagents separately in the first and second compartments, and allows for introduction of the sample into the container and the mixing of the sample with the first reagent and the second reagent within the container. The device also includes a system for optically determining the amount of a development of a color change in the mixture of the sample, the first reagent and the second reagent. The device can also include a third compartment for receiving the first reagent, the second reagent and the serum sample. The system for optically determining the amount of a development of a color change is a set of colorimetric standards for relating a color change in a mixture. In certain aspects, example, the system may be a color chart having a plurality of colors for correlating a color change to an amount of pancreatic lipase in the sample.

In another aspect, the invention is directed to a method that includes providing a device having a container with a first compartment containing a first reagent of a chromogenic lipase substrate, and a second compartment containing a second reagent comprising surface active agent. One or both of the first reagent or the second reagent include a colipase. The container stores the first and the second reagents separately in the first and second compartments, and the container allows for introduction of the serum sample into the container. The sample, the first reagent and the second reagent are mixed within the container. The device also includes a system for optically determining the amount of a development of a color change in the mixture of the sample, the first reagent and the second reagent.

In one particular aspect of the method if the invention, the sample is introduced into the container and mixed with the first reagent and the second reagent within the container. The color change in the mixture is determined and correlated to the presence or amount of pancreatic lipase in the sample.

Still further, the invention is directed to a device having a spreading layer, a a first reagent layer comprising colipase, deoxycholate, and calcium, a second reagent layer comprising DGGR substrate, and a system for optically determining the amount of a development of a color change in the mixture of the sample, the first reagent and the second reagent. In the method of the invention using this device, the sample is introduced onto the spreading layer. Color change is determined in the reagent layer and correlated to the presence or amount of pancreatic lipase in the sample.

DETAILED DESCRIPTION

In one aspect, the invention is directed to a device for a rapid and specific patient-side calorimetric assay for pancreatic lipase in a test serum sample. The device includes a compartmentalized container that stores all of the reagents that are necessary for the assay in two or more separate compartments. In another aspect, the method is directed to a multilayer device having reagents for detecting pancreatic lipase dried in the various layers.

In one aspect, the assay reagents include the DGGR substrate and a colipase. The use of the DGGR substrate provides a specific colorimetric signal in the presence of pancreatic lipase. The performance of an assay using the DGGR substrate is dependent, in part, upon the storage of the reagents. In a particular aspect of the invention, the DGGR substrate and a colipase are stored separately until the point of use. The separate storage compartments of the device prevent the mixing of the reagents until the device is used.

In another aspect, the device provides for the onboard mixing of the separately stored reagents with the serum sample. The device may include a separate compartment for mixing the sample and reagents. Alternatively, the sample can be mixed with the reagents in one of the storage compartments, and then the mixture can combined with the other of the reagents.

The compartments of the container may be separated by one or more deformable members, such partitions, dividers, bladders and the like. The member is operatively associated with the compartments such that the deformation of the member results in the contents of one compartment being released into another compartment. Alternatively, the member may be a partition separating the compartments such that the deformation of the partition results in the formation of a single compartment. The member can be deformed in any manner, such as by destroying all or part of the member, or by fracturing or piercing the member, or by any other method that permits the introduction of the contents of one compartment into another compartment. The container may also contain channels between the compartments with the channels containing deformable members that, upon deformation, allow the contents of one of the compartments to enter another compartment.

In one aspect, the device provides for a closed container that avoids direct handling of the stored reagents. Introduction of the sample into the device, and the mixing of the sample and the reagents, can be accomplished in a number of ways. For example, the sample may be introduced into such a system through a sample entry port, such as by graduated disposable pipette or needle and syringe injection of the sample through a port into one of the compartments.

The sample may be introduced into any of the compartments, including one of the reagent storage compartments or a separate compartment. Once the sample is introduced into the device, the member or members separating the compartments can be deformed to allow the mixing with all of the on-board reagents.

When DGGR with other active ingredients are used, these reagents are stored in the device in separate compartments. Upon mixing of the reagents and the serum sample, the presence of pancreatic enzyme activity in the serum sample is indicated by the development of a red colored solution. The color intensity is directly proportional to the lipase activity in the serum sample. Such a detectable color may be measured visually, with the naked eye, or spectrophotometrically.

In one aspect, the device of the invention includes a system for optically determining the amount of a development of a color change in the mixture of the sample and the reagents. The system can be as simple as a color chart that provides a gradient of color intensity that correlates to the serum lipase concentration in the reaction mixture. In operation, the user can compare the color intensity of the reaction mixture with the color chart to determine the concentration of lipase in the sample. In another embodiment, the system includes an onboard series of standard lipase concentrations in compartments that can be filled with the onboard reagents. The color development of the mixture of the sample and the reagents can be compared with the color development of the standards and the reagents. In another aspect, the color development can be determined spectrophotometrically using an instrument that can measure the color change in the solution.

The standards may be kept in their individual compartments. The reagents may be added manually to the compartments from the storage compartment of the device, or the device may be configured to allow for the reagents to be applied to the standards upon deformation of one or more members separating reagent storage compartments from the compartments containing the standards. In this respect, the device may contain several compartments containing the same reagent so that the system remains a closed system. The compartments containing the lipase standards may be connected to the reagent storage compartment or mixing compartments via one-way valves to prevent standard solutions from entering the reagent storage and mixing compartments.

The device may be formed by any material suitable for the storage and mixing of the reagents, the sample, and the onboard standards, if present. In one aspect, the device is made of a rigid plastic polymer or co-polymer, such as polyethylene. In other aspects, the device includes compartments of flexible bladder type structures that may be pierced to release reagents. The bladders may be kept within a rigid structure for ease of storage and handling. Members that maintain the reagents in their separate compartments may be constructed of similar materials but having the property of being readily deformed so as to allow mixing of the reagents and sample. In another aspect, the materials forming the compartment where the mixing of the reagent and sample occurs is a transparent or highly translucent material, or contains a window of such material, to allow for the visual or spectrophotometric determination of the color change of the mixture.

In another aspect, the invention is directed to method of detecting the presence or amount of lipase in a serum sample. The method of the invention includes mixing the serum sample with the reagents stored in the device. For example, the reagents may be stored in compartments separated by a deformable member. The sample can be added to one of the compartments and, upon deformation of the member, all of the reagents and sample are mixed. Alternatively, the reagents can be mixed prior to adding the sample. In another aspect, the method includes adding the sample to a separate compartment and the simultaneous or sequential addition of the reagents to the sample by deforming one or more members separating the compartments. Once the sample and reagents are mixed, the reaction is allowed to take place for a suitable time to allow color to develop if lipase is present in the sample. The color development is compared with the development of the color of the compartments containing the onboard standards, or to the color chart.

In one aspect, the device of the invention includes a container having at least two separate compartments, a compartment for storing a first reagent and a compartment for storing a second reagent, and at least one partition. Preferably, the body of the container is molded to form the compartments, preferably formed from a relatively rigid plastic. The compartments are separated in one embodiment by the partition, that may be constructed to be deformed, such as by destructing, fracturing or piercing and the like, permitting conjoining of the compartments to form a mixing compartment to allow mixing of the contents of the compartments. A serum sample may be delivered either directly to the mixing compartment following deformation of the portioned compartments, or the serum sample may be delivered to one of the compartments having one reagent prior to mixing with the other reagent.

The container may also include transparent sections for ready determination of a result. For example, the container may be made from a lightweight inexpensive see-through plastic, such as polyethylene, which is liquid and gas impermeable, that allows liquids within to be visible without distortion of true color.

In another embodiment, a rigid outer container enclosing the compartmentalized container includes a desiccant, and can be easily dismantled to provide access to the compartmentalized container, which are preferably encased in a sleeve having markings and instructions thereon, or such markings or instructions may be provided as a separate insert within the outer container.

At least the portion of the container where mixing of the reagents and the serum sample takes place is transparent to allow visibility of a developing color as a measure of the lipase activity. In one aspect, the compartmentalized container has attached, appended or is accompanied by a standards chart for visual comparison of color intensity of the mixture of the reagents and sample.

In one aspect, the assay is based upon the cleavage by the catalytic action of alkaline lipase solution of specific chromogenic lipase substrate DGGR, emulsified with bile acids, as described in U.S. Pat. No. 4,988,496, which is incorporated herein by reference in its entirety. This substrate is specific for pancreatic lipase in the presence of a colipase, which activates pancreatic lipase, but not other lipolytic enzymes found in serum. The DGGR reagent and colipase are available from Roche Diagnostics GmbH, (Mannheim, Germany). For optimal performance, the DGGR substrate and the other active ingredients must be stored separately until the point of use.

In the device of the invention, a first compartment contains the DGGR substrate in a solution having a pH of about 3.5-4.5. A second compartment contains additional reagents at a pH of around 7.5-9.0. Upon mixing of the reagents in the device, the DGGR substrate is cleaved by the catalytic action of the alkaline lipase solution to form 1,2-O-dilauryl-rac-glycerol and an unstable intermediate, glutaric acid-(6-methylresorufin) ester. Reagent concentrations and buffers may be optimized to allow the mixture that results from the combination of the reagents in each compartment to be an alkaline solution.

In one aspect, the DGGR reagent (Reagent 1) is emulsified with a bile acid salt, such as a cholate, in a buffer. The DGGR is present in a concentration of about 0.2 to about 1.0 mM/L. The bile acid salt is, for example, an alkali metal salt of cholic acid, taurocholic acid, desoxycholic acid, taurodesoxycholic acid, glyco-desoxycholic acid in amount of from about 2 to about 50 mg/ml. In one aspect the buffer is an acidic buffer such as a tartrate buffer at 10 mmol/L, pH. 4.0. Depending on the buffer, the pH of the DGGR reagent is maintained at a pH of about 3.5 to about 4.5.

Reagent 1 may also include urea in an amount of about 1 to about 100 mg/ml, a detergent, and a preservative, such as alkali metal azide, thiozide or sulphur-containing preserving agents in an amount of about 0.001 to about 2 mg/ml.

The colipase containing reagent (Reagent 2), includes buffer, a colipase and a surface active agent such a bile acid salt. In one aspect, the buffer is a 50 mM BICIN buffer at a pH of 8.0, the colipase is a porcine pancreatic colipase in an amount of at least about 1 mg/l, and the surface active agent is 1.6 mM sodium deoxycholate. Also included is 10 mM calcium chloride. Colipase free from impurities is especially preferred. Optionally included with the first reagent is a detergent and a preservative. The preservative may be selected from alkali metal azides, thiozide and sulphur-containing preserving agents and is present in first and second reagents in an amount of about 0.001 to about 2 mg/ml.

As buffer substance, there can be used all known buffers which are able, in the reagent according to the present invention, to adjust a pH value of from about 7.5 to 9.0. Examples of appropriate buffers include diethanolamine buffer, triethanolamine buffer, tris buffer and Good buffers, such as hepes buffer, taps buffer, CHES buffer (2-(cyclohexylamino)-ethanesulphonic acid) and BICIN. Generally, the amount of buffer substance is from 1 to 50 mg/ml. Salts in addition to calcium chloride may be used, for example, alkali metal, alkaline earth metal and ammonium salts, preferably in concentrations of from about 0.1 to about 10 mg/ml.

As preserving agents, in the scope of the present invention, those are used which do not impair the enzymatic activity of the lipase to be determined. Especially preferred are the alkali metal azides and particularly sodium azide. Other preserving agents, for example thiozide and other sulphur-containing preserving agents can also be used. The preferred amount of preserving agent is from about 0.001 to about 2 mg/ml.

In another aspect of the invention, Reagent 1 includes the DGGR substrate in a concentration of about 0.24 mmol/L, and $CaCl_2$ in a concentration of about 0.1 mmol/L. This reagent is stored separately in the device of the invention from Reagent 2, which includes a colipase, such as porcine pancreas colipase, at a concentration of about 0.98 mg/L, a bile acid salt such as deoxycholate in a concentration of about 1.8 mmol/L and taurodeoxycholate in a concentration of about 7.2 mmol/L. In this aspect, the pH of Reagent 1 is about 8, and the pH of reagent 2 is about 4. As a variation on this aspect, the colipase may be present in Reagent 1, which may also include sodium potassium tartrate in place of the $CaCl_2$, which is instead present in Reagent 2 along with Tris at a concentration of about 41 mmol/L. In this variation the pH of Reagent 1 is about 4.25 and the pH of Reagent 2 is about 8.5.

In another aspect, at least one of the reagents may be provided in a dry or concentrated form. Furthermore, the chromogenic lipase substrate may be incorporated into polymeric microcapsules. If the reagent according to the present invention is used in a dry or concentrated form intended for dilution to give the final composition, then it contains the mentioned substances in corresponding amount ratios, as well as preferably a protective colloid, such as polyhydroxy compounds, serum albumin, polyvinylpyrrolidone, solid polyethylene oxides and the like.

Using the invention, canine pancreatic lipase can be detected in animal blood samples, including whole blood, plasma or serum. When the sample is a serum sample, it includes a fraction, aliquot, droplet, portion, or volume of blood, taken from a patient source that is collected in the standard way using standard sampling tubes such as Li-, Na- or $NH_4$-heparin plasma. Blood samples may be centrifuged before performing the method of the invention. EDTA-, oxalate- fluoride- or citrated plasma is less desirable for storing test blood samples as they inhibit lipase activity. A test sample may be taken from any animal source, inducing canine, feline and human, using techniques known to one skilled in the art, including but not limited to, those described or referred to in "Manual of Clinical Microbiology" (6th ed.) 1995, edited by P. R. Murray, E. J. Baron, M. A. Pfaller, F. C. Tenover, and R. H. Yolken.

In yet another aspect, the invention is directed to a kit performing the assay comprising the device containing a compartmentalized container and reagents, a container for introducing the sample solution into the device, such as by graduated disposable pipette. The kit further includes instructions for use of the device. The kit components may be enclosed in a further sealed container for shipment and storage, such as a foil pouch, and may include a desiccant. The kit may also include specimen collection tubes for serum collection such as Li-, Na- or $NH_4$-heparin tubes.

The reagents according to the present invention can also be impregnated on to an appropriate carrier material, such a bibulous porous carrier. For this purpose, there can be used not only an absorbent carrier material but also a swellable, soluble, film-forming carrier material. In this form, the reagent according to the present invention makes possible the production of test strips which can be evaluated directly visually or by means of appropriate measurement apparatus. The determination itself can be carried out not only as an end point determination but also kinetically.

In one aspect, the invention provides a device for dry chemistry determination of lipase in animals. In this aspect, dry analytical elements are arranged in the form of test slides with multiple layers. Such slides are described, for example, in U.S. Pat. Nos. 3,992,158 and 4,066,403, the disclosures of which are incorporated by reference in their entirety. For example, the slide can comprise a spreading layer, a filtering layer, at least one reagent layer, and a support. The filtering layer can be composed, for example, of titanium dioxide in blushed cellulose acetate and the spreading layer can be composed of diatomaceous earth in blushed cellulose acetate or of glass beads mutually adhered with a hydrophilic colloid like gelatin.

The spreading layer spreads and meters a sample that is applied to the device. A sample that is applied to the device is distributed uniformly, preferably by one or more layers which perform this function, to provide a uniform apparent concentration at the surface of the spreading layer. The spreading layer is in contact with adjacent layer(s) so as to permit a fluid, or one or more of its components, whether liquid or gaseous, to pass or be transported between the layers. The sample spreading layer in the multilayer analytical device is generally the layer upon which the liquid sample to be analyzed is deposited. Typically, the sample can be applied to the sample spreading layer in drop form. Spreading layers are described, for example, in U.S. Pat. Nos. 3,992,158 and 4,066,403.

In certain aspects, one reagent layer comprises at least 1 mg/$dm^2$ colipase, 1-2 mmol/$dm^2$ deoxycholate, and 10 mmol/$dm^2$ calcium. Non-reactive ingredients in this layer can include detergent and preservative. The layer can be dried in buffer that has a pH between about 7.0 and about 9.0 (for example, in BICIN buffer).

In other aspects, a second reagent layer comprises DGGR substrate at about 0.1 to about 1.0 mmol/$dm^2$ and 1 to about 20 mmol/$dm^2$ taurodeoxycholate. Non-reactive ingredients that can be present in this layer can include detergent and preservative. This layer can be dried in buffer that has a pH between about 3.5 and about 4.5 (for example, in tartrate buffer). One of skill in the art will recognize that other combinations of reagents in various layers are also possible.

The support can be optionally provided, if the layers performing the other functions are not self-supporting. The support, if present, can be comprised of a radiation (preferably light) transmitting, liquid-impermeable material as described, for example, in U.S. Pat. No. 3,992,158. Layers discussed above can be coated directly on the support, or a subbing layer having energy transmission characteristics similar to those of the support may be used to aid in bonding the reagent layer to the support. Alternatively, the support can be eliminated, particularly in those instances in which the binder of at least one of the other layers is self-supporting. In addition, the device can include a filtering layer that can remove unwanted particulate from the sample. For example, the filtering layer can remove red blood cells to prevent the cells from interfering with the determination of the development of a color in a reagent layer.

In certain aspects, a multiple layer dry chemistry detection device can be assembled in a slide format, or any other format that provides a vehicle for dry chemistry.

In certain aspects of the invention, a sample is placed on the spreading layer of a dry chemistry detection device. When lipase is present in the sample, the DGGR substrate provides a specific colorimetric signal, which produces a change in optical density that can be sensed by a reflectometer or other device, the amount of light reflected from the element varying in accordance with the reaction and being indicative of the amount of a particular component present in the fluid. For example, light can be emitted through the support (if a support is used) to the reagent layer(s), the light can be reflected to a detector device, which measures a colorimetric change that indicates the presence of lipase in a sample. One exemplary chemical analyzer that can be used in this manner to detect lipase on a multiple layer dry chemistry device is described in U.S. Pat. No. 5,250,262, which is incorporated by reference herein in its entirety.

The following example describes the measurement of lipase in a serum sample using a kit containing a lipase kinetic assay. The lipase activity of the samples is calibrated with a lipase calibrator included in the kit.

EXAMPLE 1

It has been determined that for serum lipase assays using the DGGR substrate that results are linear between 2 and 400 U/L of pancreatic lipase. Thus, controls for a normal range of lipase activity are established between 2 and 42 U/L, and controls for an abnormal lipase activity are established between 58 and 500 U/L. Lyophilized calibrators prepared with fixed levels of lipase activity, for example, 11, 119 and 215 U/L, are prepared. These may be reconstituted with 0.5 ml of water and mixed gently until a complete solution is formed.

To develop the standards, 31 ml of a Reagent 2 including 1.8 mM deoxycholate, 7.2 mM taurodeoxycholate, 0.1 mM calcium chloride and tris buffer is mixed with 3 ml of a Reagent 1 having 0.24 mM DGGR substrate, 1 mg/L colipase and 1.6 mM sodium potassium tartrate for form a solution. 1 ml of each reconstituted calibrator is added to the resultant reagents solution and the color measured by spectrophotometer at approximately 580 nm with a pathlength of 1 cm, using a distilled water sample to calibrate the spectrophotometer. A standard linear relationship between lipase concentration and color may be established.

EXAMPLE 2

A device of the invention has two separate compartments containing a Reagent 1 and a Reagent 2. Reagent 2 contains 250 μL of a mixture of the following: 50 mmol/L BICIN buffer at pH 8.0, 1 mg/L porcine pancreas colipase, 1.6 mmol/L sodium deoxycholate, and 10 mmo/L calcium chloride with non-reactive ingredients detergent and preservative. Reagent 1 contains 150 μL of a mixture of 10 mmol/L tartrate buffer at pH 4.0, 0.27 mmol/L DGGR substrate and 8.8 mmol/L taurodeoxycholate also with non-reactive ingredients detergent and preservative. The device is manipulated to fracture the member separating Reagents 1 and 2, and the device gently shaken to allow the mixing of the two reagents. 4 μL of a serum sample collected from a canine having pancreatitis is added via an entry port to the mixed solution of Reagents 1 and 2, and the device again gently shaken to cause a reaction to take place. The resultant red coloration developed after a few seconds is measured against a color chart held up to a transparent window in the device where the colored solution can be clearly seen. The color of the reaction solution is seen to be closest to the standard (see Example 1 above) representing 119 U/L. The canine is deemed to be positive for pancreatitis.

EXAMPLE 3

Another device according to the invention has three separate compartments respectively containing 300 μL of Reagent 2 comprising 1 mg/L porcine pancreas colipase, 1.8 mmol/L sodium deoxycholate, and 7.2 mmol/L taurodeoxycholate, 60 μL of Reagent 1 comprising 0.24 mmol/L DGGR substrate and 0.1 mmol/L calcium chloride, and 3 μL of a feline serum sample previously stored in a heparin tube. The device is bent to fracture the members separating the three compartments as described above. Reaction and color measurement is carried out as described in Example 2 above.

Although various specific embodiments of the present invention have been described herein, it is to be understood that the invention is not limited to those precise embodiments and that various changes or modifications can be affected therein by one skilled in the art without departing from the scope and spirit of the invention.

What is claimed is:

1. A device for detecting the presence or amount of pancreatic lipase in an animal blood sample, the device being suitable for kit form and capable of being shaken by the user, the device comprising:
   (a) a container consisting of a first compartment containing a first liquid reagent comprising a chromogenic lipase substrate, a second compartment containing a second liquid reagent comprising a surface active agent, and an optional third compartment, wherein at least one of the first reagent or the second reagent comprises a colipase, and wherein the container stores the first and the second reagents separately in the first and second compartments, and the container allows for introduction of the sample into the container and the mixing of the sample, the first reagent and the second reagent within the container; and
   (b) a system for optically determining the amount of a development of a color change in the mixture of the sample, the first reagent and the second reagent, wherein the system comprises a color chart comprising a gradient of color intensity for visually comparing a color change in a mixture comprising the sample, the first reagent and the second reagent to an amount of pancreatic lipase in the sample.

2. The device of claim 1, wherein the pH of the first reagent is between about 3.5 and 4.5.

3. The device of claim 1, wherein the pH of the second reagent is between about 7.5 and 9.0.

4. The device of claim 1, wherein the pH of the first reagent is between about 3.5 and 4.5, and the pH of the second reagent is between about 7.5 and 9.0.

5. The device of claim 1, wherein the animal is a canine, a feline or an equine.

6. The device of claim 1, further comprising a first deformable member operatively associated the first and second compartments, wherein deformation of the first deformable member results in the mixing of the first and second reagents.

7. The device of claim 1, wherein the container comprises a sample entry port.

8. The device of claim 1, further comprising a third compartment for receiving the first reagent, the second reagent and the sample, wherein a second deformable member separates the first compartment and the third compartment, and a third deformable member separates the second compartment and the third compartment.

9. The device of claim 1, wherein the system for determining the amount of development of a color change comprises a set of standard concentrations of pancreatic lipase.

10. The device of claim 1, wherein the chromogenic lipase substrate is 1,2-O-dilauryl-rac-glycero-3-glutaric acid-(6-methyl-resorufin)ester (DGGR).

11. The device of claim 1, wherein the surface active agent is a bile acid salt.

12. The device of claim 1, wherein the surface active agent is taurodeoxycholate in an concentration of about 7 and 9 mM.

13. The device of claim 1, wherein the first reagent further comprises taurodeoxycholate in a concentration of about 7 and 9 mM.

14. The device of claim 1, wherein the first reagent or the second reagent further comprises $CaCl_2$ in a concentration of between about 0.1 and 10 mm01/L.

15. The device of claim 1, wherein the at least one of the first reagent and the second reagent comprises colipase in an amount of about 1 mg/L.

16. A kit comprising, the device of claim 1, at least one container for introducing a fluid sample into the device, and instructions for use of the device.

17. The device of claim 1, wherein the first reagent but not the second reagent comprises the colipase.

18. The device of claim 1, wherein the second reagent but not the first reagent comprises the colipase.

19. The device of claim 6, wherein the first deformable member is a partition separating the first and second compartments.

20. The device of claim 10, wherein the DGGR is in an amount of about 0.22 mmol/L to about 0.30 mmol/L.

21. The device of claim 11, wherein the bile acid salt is a cholate.

22. A method for detecting the presence or amount of pancreatic lipase in an animal sample comprising:
   a. providing a device suitable for kit form and capable of being shaken by the user, the device comprising:
      i. a container consisting of a first compartment containing a first liquid reagent comprising a chromogenic lipase substrate, a second compartment containing a second liquid reagent comprising a surface active agent, and an optional third compartment, wherein at least one of the first reagent or the second reagent comprises a colipase, and wherein the container stores the first and the second reagents separately in the first and second compartments, and the container allows for introduction of the sample into the container and the mixing of the sample, the first reagent and the second reagent within the container; and ii. a color chart for visually determining the amount of a development of a color change in the mixture of the sample, the first reagent and the second reagent, b. introducing the sample into the container;

c. mixing a sample with the first reagent and the second reagent within the container; and d. determining a color change in the mixture by visually comparing the color of the mixture to the color chart.

23. The device of claim 22, wherein the pH of the first reagent is between about 3.5 and 4.5 and the pH of the second reagent is between about 7 and 9.

24. The device of claim 22, wherein a deformable member operatively associated with the first and second compartments is deformed to mix the first and second reagents.

25. The device of claim 22, wherein the sample is introduced into one of the first and the second compartments.

26. The device of claim 22, wherein the sample is introduced into a mixing compartment created by the deformation of the member.

27. The device of claim 22, wherein the container comprises a third compartment and the method further comprises releasing the first reagent and the second reagent into the third compartment for mixing with the sample.

28. The device of claim 22, wherein the animal is a canine, a feline or an equine.

29. A device for detecting the presence or amount of pancreatic lipase in an animal blood sample, the device being suitable for kit form and capable of being shaken by the user, the device comprising:

(a) a container consisting of a first compartment containing a first liquid reagent comprising a chromogenic lipase substrate in a solution having a pH of about 3.5-4.5, a second compartment containing a second liquid reagent comprising a surface active agent in a solution having a pH of about 7.5-9.0, and an optional third compartment, and wherein the container stores the first and the second reagents separately in the first and second compartments, and the container allows for introduction of the sample into the container and the mixing of the sample, the first reagent and the second reagent within the container; and (b) a system for visually determining the amount of a development of a color change in the mixture of the sample, the first reagent and the second reagent, wherein the system comprises a color chart that provides a gradient of color intensity that correlates to the serum lipase concentration in the sample, wherein the color chart can be visually compared to the sample following its introduction to the first and second reagents.

30. A method for detecting the presence or amount of pancreatic lipase in an animal sample comprising:

(a) providing a device suitable for kit form and capable of being shaken by the user, the device comprising:

i. a spreading layer, a first reagent layer comprising colipase, deoxycholate and calcium, and a second reagent layer comprising a DGGR substrate, and ii. a color chart providing a gradient of color intensity for visually determining the amount of a development of a color change in the mixture of the sample, the first reagent and the second reagent;

(b) introducing the sample onto the spreading layer; and (c) determining the presence or amount of pancreatic lipase in the sample by visually comparing the amount of color development in the mixture with the color chart.

31. The method of claim 30, wherein the first reagent layer is dried in a buffer that has a pH between about 7.0 to about pH 8.0.

32. The method of claim 30, wherein the second reagent layer is dried in a buffer that has a pH between about 3.5 and 4.5.

33. The method of claim 30, wherein the device further comprises a filtering layer.

34. The method of claim 30, wherein the device further comprises a support layer.

35. A device for detecting the presence or amount of pancreatic lipase in an animal sample comprising:

(a) a spreading layer;

(b) a first reagent comprising colipase, deoxycholate, and calcium;

(c) a second reagent layer comprising DGGR substrate; and (d) a system for optically determining the amount of a development of a color change in the mixture of the sample, the first reagent and the second reagent, wherein the system comprises a visually readable color chart that provides a gradient of color intensity that correlates to the serum lipase concentration in the sample, wherein the device is suitable for kit form and is capable of being shaken by the user.

36. The device of claim 35, wherein the first reagent layer is dried in a buffer that has a pH between about 7.0 to about pH 8.0.

37. The device of claim 35, wherein the second reagent layer is dried in a buffer that has a pH between about 3.5 and 4.5.

38. The device of claim 35, further comprising a filtering layer.

39. The device of claim 35, further comprising a support layer.

* * * * *